US00PP31003P2

(12) United States Plant Patent
Olesen

(10) Patent No.: US PP31,003 P2
(45) Date of Patent: Nov. 5, 2019

(54) **COMPACT FLORIBUNDA *ROSA* PLANT NAMED 'POULPAL073'**

(50) Latin Name: ***Rosa* hybrid**
Varietal Denomination: Poulpal073

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,585

(22) Filed: Sep. 4, 2018

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749; A01H 5/02
See application file for complete search history.

*Primary Examiner* — Keith O. Robinson

(57) ABSTRACT

A new garden rose plant of the Compact Floribunda class which has abundant, red-purple flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal073'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal073', originated as a single seedling from the stated cross.

The new variety may be distinguished from its male pollen parent and female seed parent primarily by the following characteristics. The male pollen parent plant has a growth height of 100 cm, while the new variety has a growth height of 50 cm. The female seed parent plant has orange flowers while the new variety has red-purple flowers.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance.

This combination of qualities is not present in previously available commercial cultivars of this type, known to the inventor, and distinguish 'Poulpal073' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal073' was selected in the spring of 2008 by the inventor as a single plant from the progeny of the aforementioned hybridization.

Asexual reproduction of 'Poulpal073' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpal073' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal073'.

Specifically illustrated in FIG. 1 of the drawings is an open flower viewed from the side and above, flower petals detached, showing reproductive flower parts, sepals detached, a cluster of flower buds on a branch, and flower buds detached.

Figure 1:
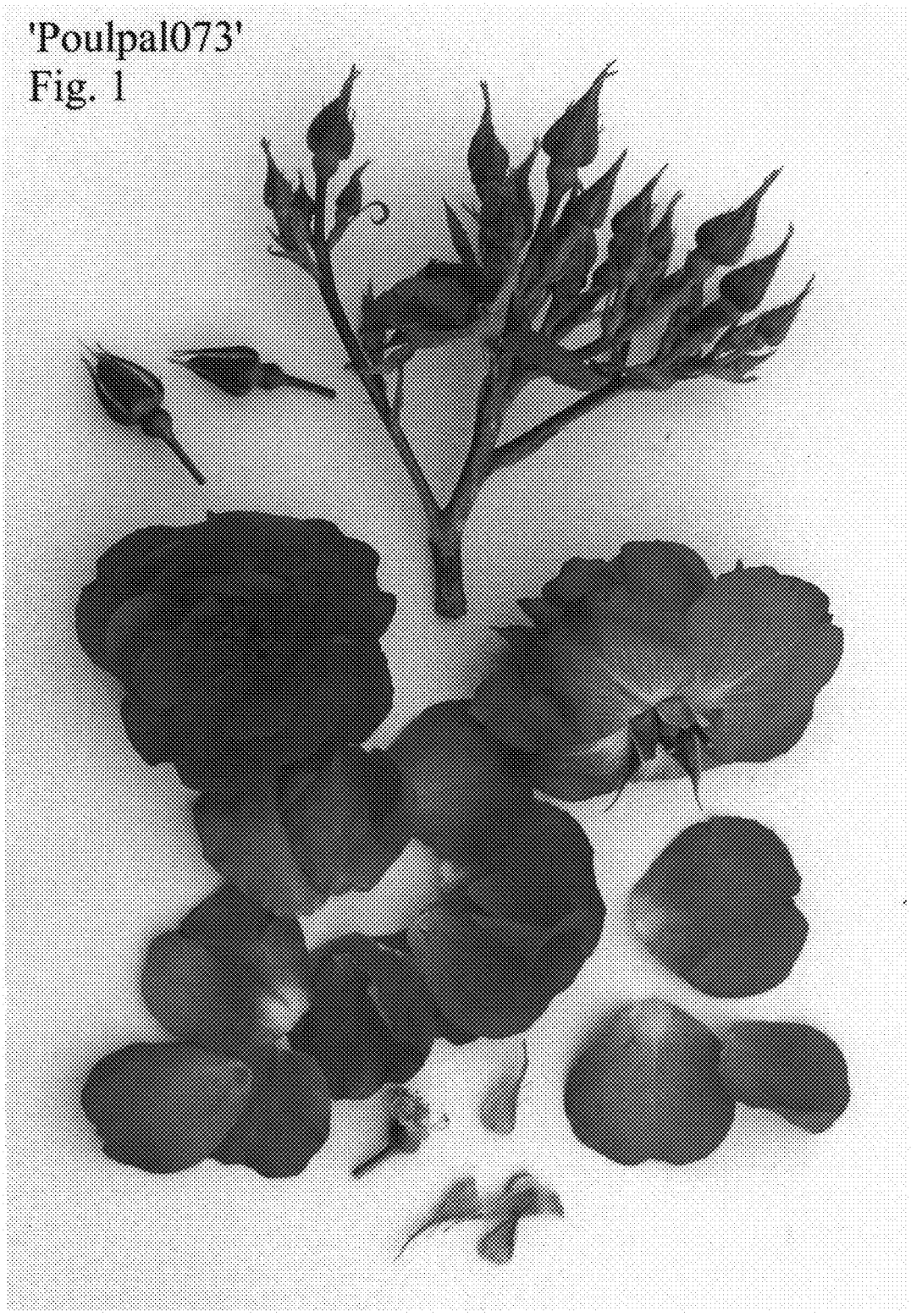
Figure 2:
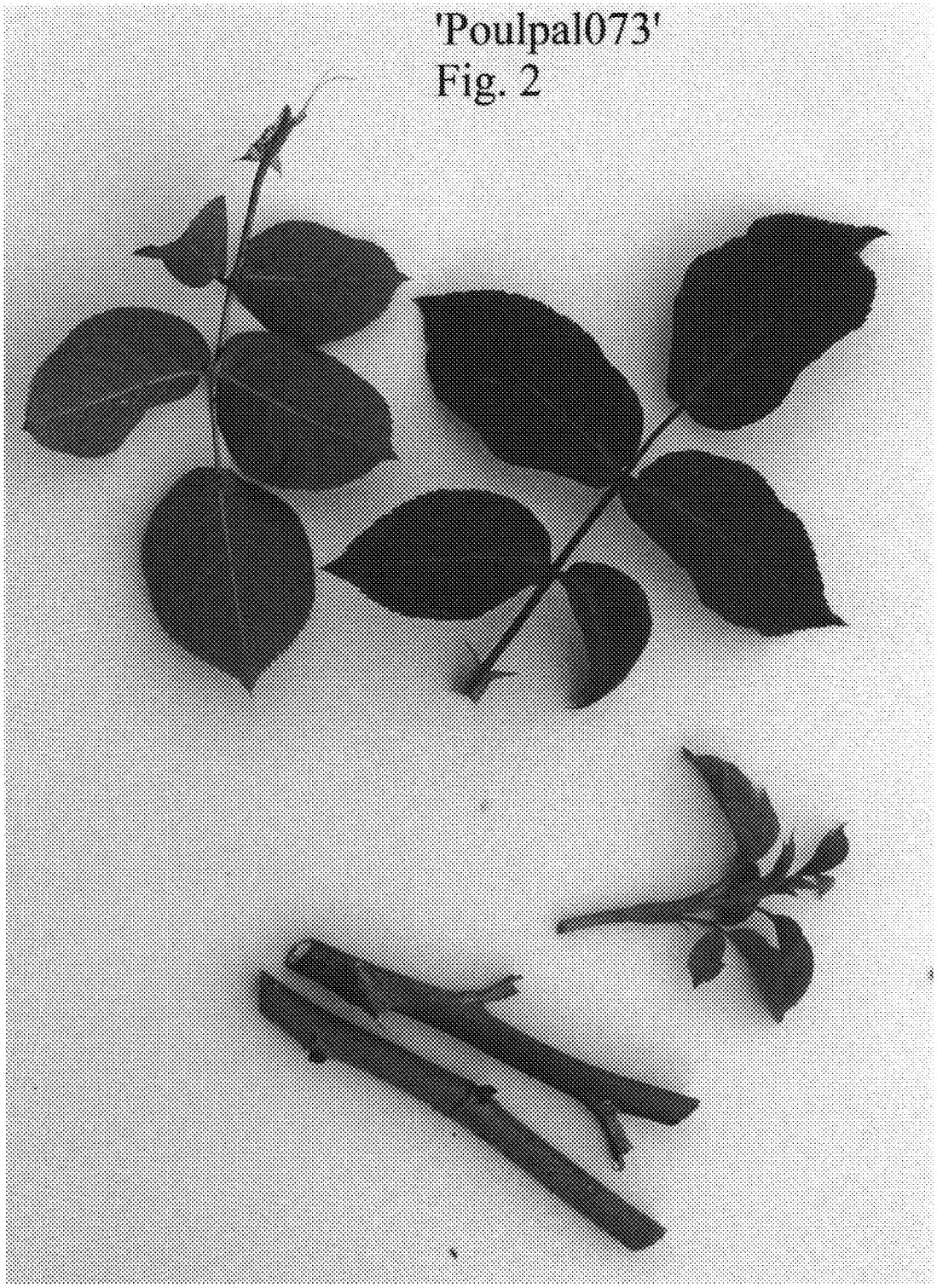

Specifically illustrated in FIG. 2 of the drawings are mature leaves, juvenile growth, and bare stems. Plants shown are 2 years of age.

DETAILED DESCRIPTION OF THE VARIETY

The following is a description of 'Poulpal073',as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulpal073' in Chart 1.

CHART 1

| | 'Poulpal073' | 'Poulcas031' |
|---|---|---|
| Petal Count | 18 | 40-50 |
| Flower Diameter | 100 mm | 70-80 mm |
| General Tonality of Flower Color | Red-Purple Group 60A | Red-Purple Group N 57A |

Flower and Flower Bud

Blooming habit: Continuous.

Flower bud:

*Size*.—Upon opening, 24 mm in length from base of receptacle to end of bud. Bud diameter is 14 mm.

*Bud form*.—Ovoid.

*Bud color*.—As sepals divide petals are Red Group 47A.

*Sepal inner surface*.—Color: Yellow-Green Group 146C. Surface: Lightly pubescent.

*Sepal outer surface*.—Color: Yellow-Green Group 144A with strong intonations of Greyed-Purple Group 183B. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—26 mm long, by 10 mm wide.

*Receptacle*.—Texture: Smooth. Size: 8 mm in height, 9 mm wide. Color: Yellow-Green Group 144A with intonations of Greyed-Purple Group 183A. Shape: Globular.

*Pedicel*.—Surface: Smooth. Length: 25 mm. Diameter: 2 to 3 mm. Color: Yellow-Green Group 144A with intonations of Greyed-Purple Group 183A. Strength: Strong.

*Peduncle*.—Length: 20 to 40 cm. Diameter: About 4 mm. Color: Yellow-Green Group 144A with intonations of Greyed-Purple Group 183A. Texture: Smooth.

Flower bud development: Flower buds are borne in clusters of 3 to 5 flower buds on each peduncle An entire flowering branch can produce 25 to 30 flower buds.

Flower bloom:

*Fragrance*.—Moderate floral scent.

*Duration*.—The blooms have a duration on the plant of approximately 10 days. Petals fall cleanly away from plant after flowers have fully matured.

*Size*.—Flower diameter is 100 mm when open. Flower depth is 35 mm.

*Flower shape*.—Open cup double flower, with petals that curve out from the center.

*Shape of flower, side view*.—The upper portion is flat convex. The lower portion is concave.

Petalage: Under normal conditions, flowers have about 18 petals.

General tonality of flower: Open flowers are Red-Purple Group 60A.

Petal color:

*Upon opening, outer petals*.—Upper surface: Red-Purple Group 61B. Lower surface: Red-Purple Group 61C with splashed of Red-Purple Group 62B.

*Upon opening, inner petals*.—Upper surface: Red-Purple Group 61B. Lower surface: Red-Purple Group 61C with splashed of Red-Purple Group 62B.

*Basal petal spots, upon opening*.—Upper surface: Yellow Group 4D. Lower surface: Yellow Group 4D.

*After opening, outer petals*.—Upper surface: Red-Purple Group 61B. Lower surface: Red-Purple Group 61C with splashed of Red-Purple Group 62B.

*After opening, inner petals*.—Upper surface: Red-Purple Group 61B. Lower surface: Red-Purple Group 61C with splashed of Red-Purple Group 62B.

*Basal petal spots, after opening*.—Upper surface: Yellow Group 4D. Lower surface: Yellow Group 4D.

Petals:

*Petal reflex*.—None.

*Margin*.—Uniform, with a shallow cleft at the apex. Weak undulations.

*Shape*.—Broad and elliptic. Apex shape: Rounded. Base shape: Acute.

*Size*.—50 mm (l)×55 mm (w).

*Texture*.—Smooth.

*Thickness*.—Average.

Petaloids: None observed.

Reproductive flower parts:

*Pollen*.—None observed.

*Anthers*.—Size: 2 mm in length. Color: Greyed-Orange Group 167B. Quantity: 45 on average.

*Filaments*.—Color: Greyed-Yellow Group 160A with intonations of Greyed-Orange Group 173B. Length: 7 mm.

*Pistils*.—Length: 5 mm. Quantity: 20 on average.

*Stigmas*.—Color: Greyed-Yellow Group 160D.

*Styles*.—Color: Greyed-Yellow Group 160D.

*Location of stigmas*.—Inferior in location relative to the length of the filaments and the height of the anthers.

*Hips*.—None Observed.

Plant

Plant growth: Upright, bushy. Plants are 65 to 75 cm in height, and 55 cm wide.

Stems:

*Color of juvenile growth*.—Yellow-Green Group 144A with intonations of Greyed-Purple Group 183B.

*Color of mature growth*.—Yellow-Green Group.

*Length*.—Canes are about 30 cm from the base of the plant to the flowering portion.

*Diameter*.—About 9 mm.

*Internodes*.—On mature canes about 35 mm between nodes.

*Surface texture*.—Young wood: Smooth. Older wood: Rough.

Long prickles: None observed.

Plant foliage:

*Compound leaf*.—150 mm (l)×115 (w).

*Quantity*.—3 leaves per 10 cm of stem on average.

*Leaf bearing angle to the stem*.—45 degrees.

*Color of juvenile foliage*.—Upper side: Yellow-Green Group N144A with intonations of Greyed-Purple Group 183A. Lower side: Yellow-Green Group 146B with intonations of Greyed-Purple Group 183B.

*Color of mature foliage*.—Upper side: Yellow-Green Group 146A. Lower side: Yellow-Green Group 147C.

Plant leaves and leaflets:

*Stipules*.—Size: 15 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm. Upper surface color: Yellow-Green Group 144A and Greyed-Purple Group 183B. Lower surface color: Yellow-Green Group 144B and Greyed-Purple Group 183B.

*Rachis*.—Length: 60 mm. Diameter: 2 mm. Upper surface color: Yellow-Green Group 144A and Greyed-Purple Group 183B. Lower surface color: Yellow-Green Group 144B.

*Leaflet*.—Quantity: Normally 5 leaflets. Margins: Serrated. Size: Terminal leaflets are about 65 mm long, 40 mm wide. Shape: Generally elliptical. Base: Rounded. Apex: Mucronate. Texture: Smooth. Thickness: Above average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal073', substantially as illustrated and described herein, due to its abundant red-purple flowers, disease resistance, and extended period of bloom.

* * * * *

'Poulpal073'

'Poulpal073'